United States Patent
Pannek, Jr.

[11] Patent Number: 5,176,693
[45] Date of Patent: Jan. 5, 1993

[54] BALLOON EXPANDABLE ATHERECTOMY CUTTER

[75] Inventor: Edward J. Pannek, Jr., Oceanside, Calif.

[73] Assignee: InterVentional Technologies, Inc., San Diego, Calif.

[21] Appl. No.: 881,426

[22] Filed: May 11, 1992

[51] Int. Cl.⁵ ............................................. A61B 17/22
[52] U.S. Cl. ...................................... 606/159; 604/22
[58] Field of Search ............. 606/159, 170, 180, 200, 606/167; 604/22, 96–103; 15/104.03, 104.09; 128/898, 751–755

[56] References Cited

U.S. PATENT DOCUMENTS

| | | | |
|---|---|---|---|
| 2,688,329 | 9/1954 | Wallace | 128/349 |
| 2,854,983 | 10/1958 | Baskin | 604/96 |
| 3,400,708 | 9/1968 | Scheidt | 128/2 |
| 3,512,519 | 5/1970 | Hall | 128/2 |
| 3,605,721 | 8/1971 | Hallac | 128/2 B |
| 3,605,725 | 9/1971 | Bentov | 128/2.05 |
| 3,618,614 | 11/1971 | Flynn | 128/348 |
| 3,913,568 | 10/1975 | Carpenter | 128/11 |
| 3,990,453 | 11/1976 | Douvas et al. | 128/305 |
| 4,195,637 | 4/1980 | Grüntzig et al. | 128/348 |
| 4,273,128 | 6/1981 | Lary | 606/167 |
| 4,307,722 | 12/1981 | Evans | 128/344 |
| 4,441,509 | 4/1984 | Kotsifas et al. | 128/757 |
| 4,545,390 | 10/1985 | Leary | 128/772 |
| 4,571,240 | 2/1986 | Samson et al. | 604/96 |
| 4,582,181 | 4/1986 | Samson | 128/348 |
| 4,589,412 | 5/1986 | Kensey | 128/305 |
| 4,690,140 | 9/1987 | Mecca | 128/305 |
| 4,696,667 | 9/1987 | Masch | 604/22 |
| 4,708,147 | 11/1987 | Haaga | 128/753 |
| 4,728,319 | 3/1988 | Masch | 604/22 |
| 4,732,154 | 3/1988 | Shiber | 128/305 |
| 4,754,755 | 7/1988 | Husted | 128/305 |
| 4,757,826 | 7/1988 | Abdulhay | 128/757 |
| 4,765,332 | 8/1988 | Fischell et al. | 128/305 |
| 4,787,388 | 11/1988 | Hofmann | 128/344 |
| 4,886,061 | 12/1989 | Fischell et al. | 606/159 |
| 4,887,613 | 12/1989 | Farr et al. | 606/159 |
| 4,896,669 | 6/1990 | Bhate et al. | 606/194 |
| 4,950,277 | 8/1990 | Farr | 606/159 |
| 4,966,604 | 10/1990 | Reiss | 606/159 |
| 4,986,807 | 1/1991 | Farr | 604/22 |
| 5,100,425 | 3/1992 | Fischell et al. | 604/22 |

FOREIGN PATENT DOCUMENTS

| | | | |
|---|---|---|---|
| 0117519 | 2/1984 | European Pat. Off. | 606/159 |
| 3732236 | 12/1988 | Fed. Rep. of Germany | 606/159 |
| 2580504 | 10/1986 | France | 606/200 |
| 0938977 | 6/1982 | U.S.S.R. | |
| 90/00337 | 1/1990 | World Int. Prop. O. | |

Primary Examiner—C. Fred Rosenbaum
Assistant Examiner—William W. Lewis
Attorney, Agent, or Firm—Nydegger & Associates

[57] ABSTRACT

A balloon expandable atherectomy cutter for removing plaque from an artery includes an elongated cutter assembly having a plurality of blades which, with respect to the axis of rotation of the cutter, are radially separated from each other and axially aligned with each other. The assembly is mounted on the distal end of a rotatable catheter and is rotatable about a quide wire to cut plaque from an artery as it is rotated. An inflatable balloon, is mounted between an ovoid space formed between the blades. An inflator is connected with the balloon to inflate the balloon and urge it against the distal portion of the blades. In the operation of the cutter, when the balloon is deflated the blades establish a first radius of rotation which cuts through the plaque of a stenotic segment as the cutter is advanced into the artery. When the balloon is inflated, the blades are urged by the balloon into an expanded configuration wherein the blades establish a second radius or rotation, larger than the first radius, in order to cut plaque from the stenotic segment as the cutter is withdrawn from the artery.

18 Claims, 2 Drawing Sheets

BALLOON EXPANDABLE ATHERECTOMY CUTTER

FIELD OF THE INVENTION

The present invention pertains generally to medical devices which are useful for removing plaque from a stenotic segment of an artery of a patient. More particularly, the present invention pertains to atherectomy devices which cut plaque from an artery. The present invention is particularly, but not exclusively, useful as an atherectomy cutter which has balloon expandable blades for varying the cutting radius of the device.

BACKGROUND OF THE INVENTION

It is well known that any significant reduction or restriction in the flow of blood through the arteries of the body can cause complications which may have serious consequences. In any event, it is extremely important for the health of the patient that any stenosis, or blockage, which is causing such a condition be eliminated. One well known and frequently used procedure to accomplish this task is popularly known as angioplasty. For a basic angioplasty procedure, a dilatation balloon is positioned across the particular stenotic segment and the balloon is inflated to open the artery by breaking up and compressing the plaque which is creating the stenosis. The plaque, however, remains in the artery and is not removed. Unfortunately, in some cases, it appears that the plaque which remains in the artery may cause another stenosis to form.

As an alternative to angioplasty, atherectomy procedures have been developed to resolve the problems caused by blocked arteries. However, unlike an angioplasty procedure which only opens the stenosis in the artery but does not remove the plaque which caused the stenosis, in accordance with an atherectomy procedure the plaque which is creating the stenosis is mechanically cut from the artery and then removed. The cutting devices which are used for this task must, of necessity, be rather small. On the other hand they must have sufficient structural strength to cut the plaque during performance of the atherectomy procedure. Additionally, they must be operationally reliable. Many examples of such cutting devices can be given. For instance, U.S. Pat. No. 4,895,166 which issued to Farr et al. for an invention entitled "Rotatable Cutter for the Lumen of a Blood Vessel", and which is assigned to the same assignee as the present invention, discloses such a cutter. U.S. Pat. No. 4,589,412 which issued to Kensey for an invention entitled "Method and Apparatus for Surgically Removing Remote Deposits" is but another example.

One problem which must be confronted in any procedure, whether it be an angioplasty or an atherectomy procedure, is the size of the entry site that can be used for introducing the medical device into the artery. Standard practices accept an entry site which has a diameter of only approximately twelve French, i.e. about four millimeters. Thus, any device which is to be positioned in the artery must pass through an introducer whose outer diameter is not larger than twelve French. The inner diameter of such an introducer is generally, however, on the order of only nine French. The consequence is that any device which is effectively insertable into the artery of a patient must be capable of assuming a configuration wherein the greatest dimension across the device is no more than approximately seven French.

It happens, however, that to properly clear a stenotic segment it is sometimes necessary to create a lumen which has a greater diameter than seven French. To do this by an atherectomy procedure, the cutter being used must be capable of expanding beyond the seven French restriction imposed at the entry site.

Several examples of expandable cutting devices which are specifically useful as medical devices for atherectomy procedures can be given. U.S. Pat. No. 4,966,604 which issued to Reiss for an invention entitled "Expandable Atherectomy Cutter with Flexibly Bowed Blades", and U.S. Pat. No. 4,986,807 which issued to Farr for an invention entitled "Atherectomy Cutter with Radially Projecting Blade", both of which patents are assigned to the same assignee as the present invention, pertain to expandable atherectomy cutters. There is, of course, still a need for other expandable atherectomy cutters which can meet the specific needs of a specifically desired protocol.

The present invention recognizes that several factors need to be considered when determining the most desirable structure for an expandable atherectomy cutter and its method of use. First, there is the need to satisfy the personal preferences of the particular surgeon who is to perform the atherectomy operation. Clearly, different surgeons can have different approaches to the solution of the same problem. Further, there is the need to provide a structure which is best suited for performance of the particular task. It happens that atherectomy procedures can be performed in the coronary arteries, the carotid arteries, the renal arteries, and in the peripheral arteries. Each set of arteries is different and presents different challenges to the atherectomy procedure. The present invention provides such a structure for consideration and use by the operating physician.

In light of the above it is an object of the present invention to provide a compressible/expandable atherectomy cutter which can be reconfigured within an artery by manipulations performed externally of the patient. Another object of the present invention is to provide a compressible/expandable atherectomy cutter which can be configured into an operational rigid cutting configuration. Still another object of the present invention is to provide a compressible/expandable atherectomy cutter which is capable of making a reliable transition between a compressed configuration and an expanded configuration. Yet another object of the present invention is to provide a compressible/expandable atherectomy cutter which expands into a structurally predictable configuration. Another object of the present invention is to provide a compressible/expandable atherectomy cutter with is relatively simple to use, relatively easy to manufacture, and comparatively cost effective.

SUMMARY OF THE INVENTION

A balloon expandable atherectomy cutter, in accordance with the present invention, includes a hollow wire which is formed with a lumen and which has an orifice extending from the lumen through the side of the wire. An inflatable balloon is mounted on the wire to surround the orifice and position the balloon in fluid communication with the lumen of the wire. A grommet is slidingly positioned on the wire distally from the balloon, and a rotatable catheter is positioned proximally therefrom. A cutter assembly defines a substantially ovoid shaped space and is journaled for rotation by the rotatable catheter about the hollow wire.

The cutter assembly of the present invention includes a plurality of spaced-apart flexible blades which are disposed to define the ovoid space. Preferably, there are four blades with each blade being diametrically opposed to another blade and each pair of opposed blades defining a plane which is substantially perpendicular to the plane defined by the other pair of blades. Alternatively, the cutter assembly can incorporate three blades which are evenly spaced from each other. Further, each blade has a distal end which is attached to the grommet and a proximal end which is attached to the rotatable catheter.

As intended for the present invention, the cutter assembly assumes a first configuration when the balloon is deflated. In this first configuration the cutter assembly establishes a first radius of rotation for the blades. Upon inflation of the balloon, the balloon urges against the distal portion of each blade to expand the cutter assembly into a second configuration wherein the assembly establishes a second radius of rotation for the blades which is greater than the first radius of rotation. The atherectomy cutter of the present invention also includes an inflation means which is connected with the lumen of the wire to inflate the balloon and a drive means which is operatively connected to the proximal end of the rotatable catheter to rotate the catheter and the cutter assembly.

In the operation of the present invention, the cutter assembly is introduced into the artery of a patient and into contact with plaque build up in a stenotic segment of the artery. The cutter assembly is initially maintained in its first configuration, and is thus rotated and advanced through the plaque to cut and remove the plaque from the stenotic segment within the first radius of rotation. Once through the stenotic segment, the balloon is inflated to move the cutter assembly into its second configuration. The cutter assembly is again rotated and pulled or withdrawn through the stenotic segment to cut and remove plaque from the segment within the second radius of rotation. The balloon can then be deflated and, with the cutter assembly again in its first configuration, the atherectomy cutter removed from the artery of the patient. Cut plaque is evacuated by a vacuum means coupled to the rotatable catheter.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF PREFERRED EMBODIMENTS

Figure 2A:
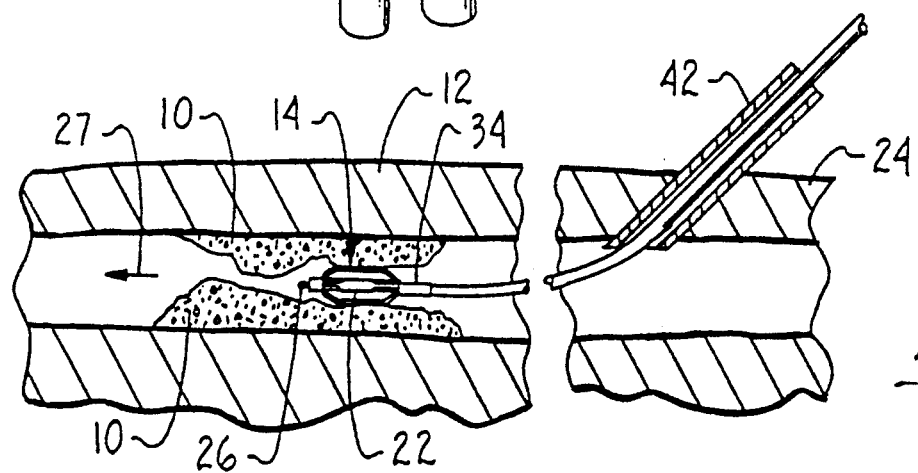
FIG. 2A is a cross-sectional view of an artery in a patient having a stenotic segment in the artery with the cutter of the present invention operationally positioned in a first configuration for cutting the stenosis with a first radius of rotation.
Figure 2B:
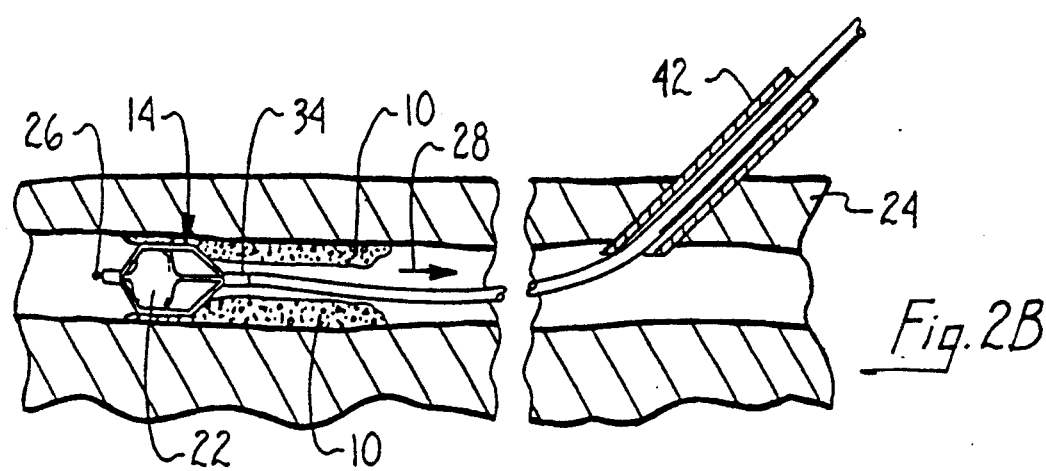
FIG. 2B is a cross-sectional view of the artery shown in FIG. 2A with the cutter of the present invention operationally positioned in a second unfiguration for cutting the stenosis with a second radius of rotation.

Referring to FIGS. 2A and 2B an atherectomy cutter system constructed in accordance with the invention is shown in use for performing an atherectomy procedure on a patient 8. The atherectomy cutter system is adapted to remove a build up of plaque 10 in a stenotic segment 12 of an artery 24 or other blood vessel of the patient 8. The atherectomy cutter system includes a balloon expandable cutter 14 rotatable by a drive means 16 for cutting through the plaque 10. The cutter is also coupled to a vacuum means 18 for evacuating and removing the broken-up plaque from the artery 24. In addition, the cutter 14 is coupled to an inflation means 20 for inflating a balloon 22 (FIG. 3) of the cutter 14 in order to increase a cutting radius of the cutter 14. The cutter system also includes a hollow guide wire 26 and the cutter 14 is rotatably mounted on the guide wire 26.

The cutter 14 is adapted to be inserted into the artery 24 of the patient 8 at an accessible location (i.e. the thigh) and guided through the artery 24 into contact with the plaque 10 formed within the stenotic segment 12. As shown in FIG. 2A the cutter 14 can then be rotated by the drive means 16 and pushed through the plaque 10 in a direction as indicated by arrow 27. As shown in FIG. 2B, the balloon 22 of the cutter 14 can then be inflated increasing the cutting radius of the cutter 14. The cutter 14 can then be pulled through the plaque 10 in a direction as indicated by arrow 28 for making a larger diameter cut through the stenotic segment 12 of the artery 24.

Figure 3:
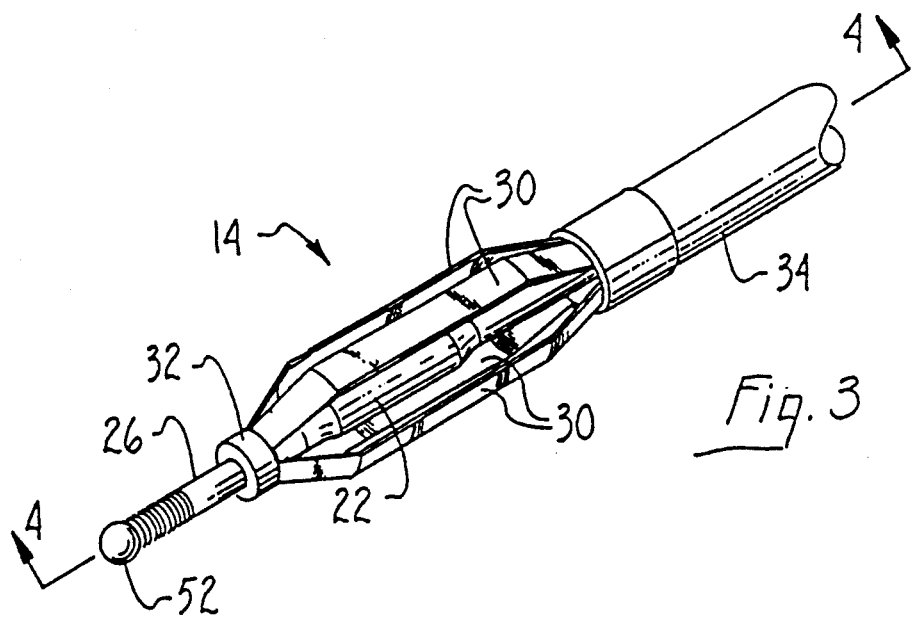
FIG. 3 is a perspective view of the balloon expandable cutter of the present invention.

With reference to FIG. 3, the cutter 14 includes four cutting blades 30. Each cutting blade 30 is diametrically opposed to another cutting blade 30. Each pair of opposed blades 30 defines a plane which is substantially perpendicular to the plane defined by the other pair of blades 30. In addition, each cutting blade 30 is attached at a distal end to a grommet 32 and at a proximal end to a hollow drive catheter 34. With this arrangement, each cutting blade 40 is journaled for rotation on the guide wire 26, supported at the distal end by the grommet 32 and at a proximal end by an end plate 46.

Figure 4A:
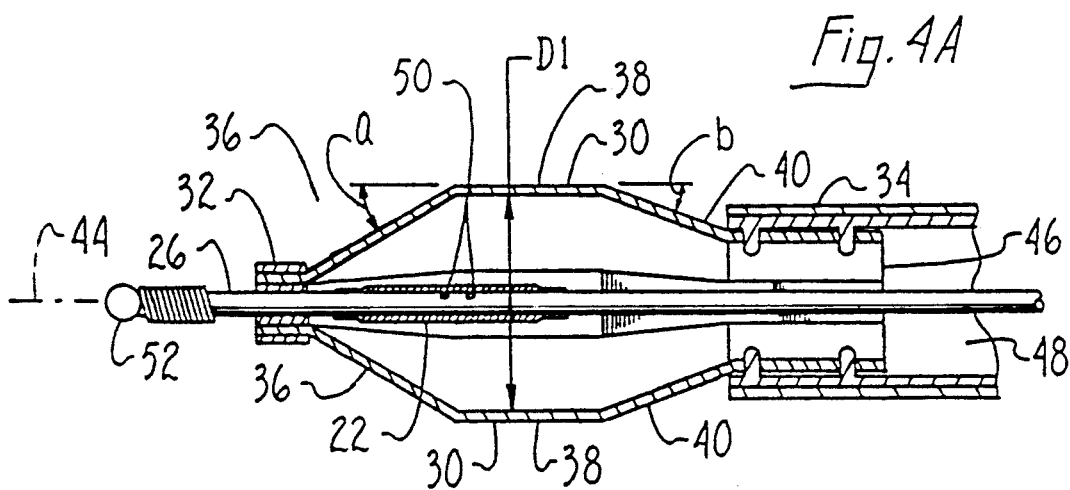
FIG. 4A is a cross-sectional view of the cutter along the line 4—4 in FIG. 3 with the cutter in a first configuration for advancement into the artery as indicated in FIG. 2A.
Figure 4B:
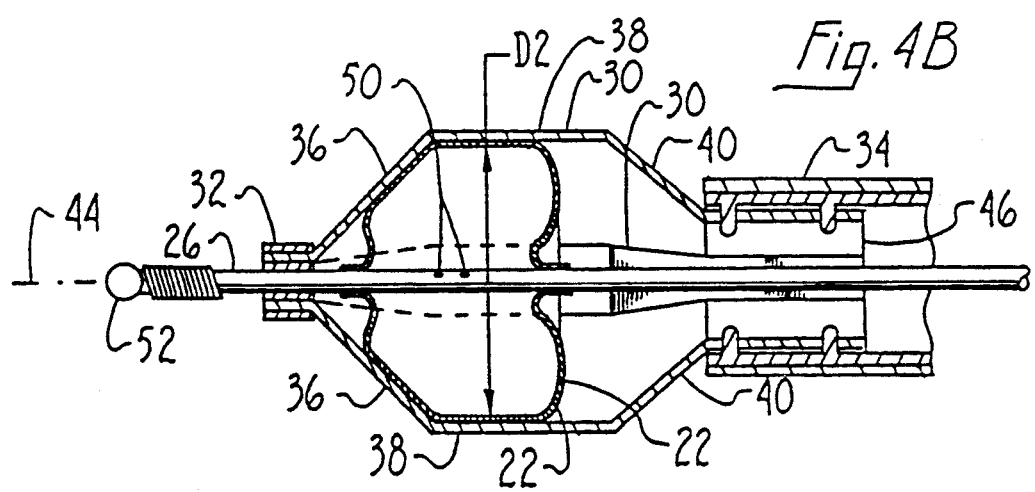
FIG. 4B is a cross-sectional view of the cutter along the line 4—4 in FIG. 3 with the cutter in a second configuration for withdrawal from the artery as indicated in FIG. 2B.

The drive catheter 34 is coupled for rotation by the drive means 16 about a rotational axis 44. Rotational axis 44 is coincident with a longitudinal axis 44 of the guide wire 26. Additionally an annular area 48 formed within the lumen of the hollow drive catheter 34 can be coupled to the vacuum means 18 (FIG. 1) to provide a conduit for removal of cut plaque 10 from the artery 24. The cutting blades 30 in an unstressed shape form a first cutting diameter D1 as shown in FIG. 4A. The cutting blades 30 are formed however, to flex under pressure from the balloon 22 to an increased cutting diameter D2 which is shown in FIG. 4B. In addition, each cutting blade 30 is formed with an advancing cutter segment 36, an intermediate cutter segment 38, and a withdrawing cutter segment 40. Each advancing cutter segment 36 is formed at an angle "a" to a longitudinal or rotational axis 44 of the cutter 14 which allows the cutter 14 to be easily pushed or advanced through the plaque 10. Likewise, the withdrawing cutter segment 40 is formed at an angle "b" to the rotational axis 44 of the cutter 14 which allows the cutter 14 to be easily pulled through the plaque 10. The intermediate cutter segment 38 is generally straight and connects the advancing cutter segment 36 and the withdrawing cutter segment 40 of the cutting blades 30. The interior area of the cutter 14 defined by the cutting blades 30 is substantially ovoid in shape.

The balloon 22 is mounted to the hollow guide wire 26 at a distal end of the guide wire 26. The hollow guide wire 26 is formed with a lumen that is coupled to the inflation means 20 (FIG. 1) for inflating the balloon 22. The lumen of the hollow guide wire 26 is coupled to one or more orifices 50 that are adapted to provide a conduit for a fluid under pressure from the inflation means 20 for inflating the balloon 22. As such the balloon 22 is sealingly attached to the guide wire 26 and over the orifices 50. The guide wire 26 is also formed with a radiopaque tip 52 and coil at its distal end to facilitate steering the cutter 14 to the stenotic segment 12 of the artery 24 using radiological techniques.

OPERATION

Figure 1:
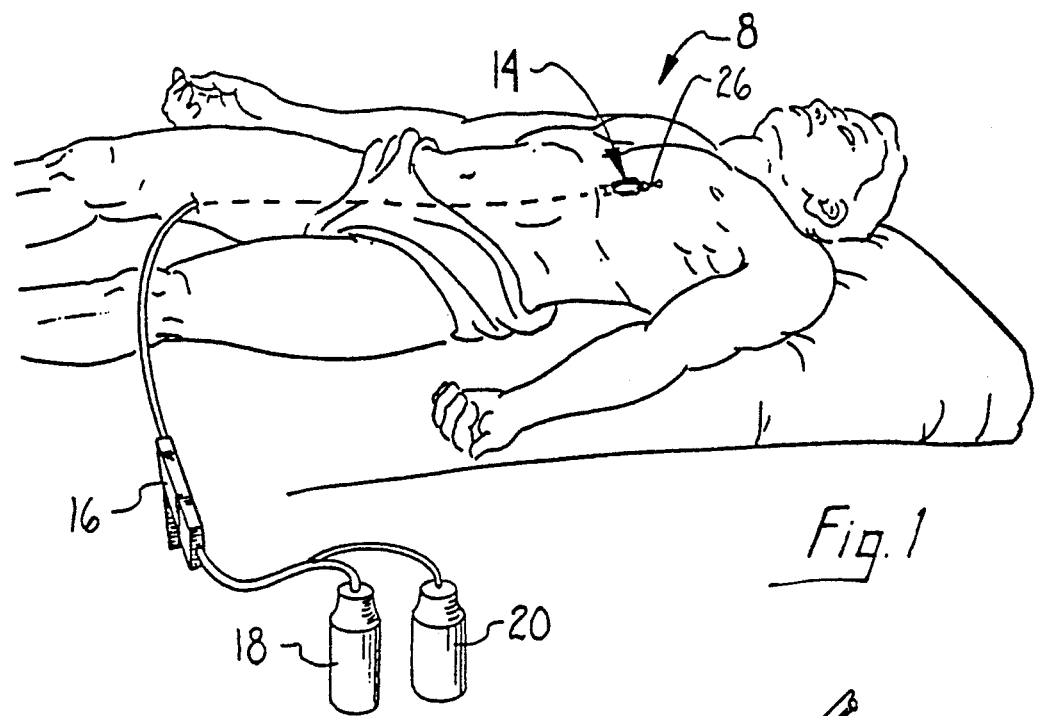
FIG. 1 is a view of an operational atherectomy system using the balloon expandable cutter of the present invention.

Referring to FIGS. 1, 2A, and 2B the atherectomy cutter of the invention can be used for removing a build up of plaque 10 in a stenotic segment 12 of an artery 24 or other blood vessel of a patient 8. The insertion catheter 42 is percutaneously introduced into an accessible location of the artery 24 such as in the patient's inner thigh. The cutter 14 is then threaded through the insertion catheter and into the artery 24 and is guided through the artery 24 to the stenotic segment 12 of the artery 24. The cutter 14 can be guided through the artery to the stenotic segment 12 utilizing radiological techniques that are known in the art and with the aid of radiopaque tip 52.

Initially, the cutter 14 is positioned adjacent to the plaque 10. Then, the drive means 16 is connected to the hollow drive catheter 34 and is activated to rotate the cutter 14. The cutter 14 is advanced through the plaque 10 with the cutting blades 30 positioned in a first configuration with a smaller cutting diameter D1. During advancement of the cutter through the plaque 10 the vacuum means 18 can be coupled to the hollow drive catheter 34 so that cut pieces of plaque 10 are drawn into the drive catheter 34 and out of the artery 24. The construction of the cutting blades 30 with advancing cutter segments 36 at a distal end thereof facilitates movement of the cutter 14 through the plaque 10. This effectively opens up the stenotic segment 12 to a diameter of D1.

Once the cutter 14 has been advanced through the plaque 10, the balloon 22 is inflated. For inflating the balloon 22, an inflation fluid is introduced under pressure by the inflation means 20 into the lumen of the guide wire 26, through the orifices 50 in the guide wire 26, and into the balloon 22. The expanded balloon 22 presses against the cutting blades 30 and positions the cutting blades 30 in a second configuration with a larger cutting diameter D2. The cutter 14 can then be pulled back (i.e. withdrawn) through the plaque 10 making a second pass through the plaque. Again cut pieces of plaque 10 are drawn by the vacuum means 18 into the hollow drive catheter 34. This effectively opens up the stenotic segment 12 to a diameter of D2. The balloon 22 can then be deflated and the cutter 14 withdrawn from the artery 12.

While the particular Balloon Expandable Atherectomy Cutter as herein shown and disclosed in detail is fully capable of obtaining the objects and providing the advantages herein before stated, it is to be understood that it is are merely illustrative of the presently preferred embodiments of the invention and that no limitations are intended to the details of construction or design herein shown other than as described in the appended claims.

I claim:

1. An atherectomy cutter which comprises:
   a hollow wire formed with a lumen;
   an inflatable balloon mounted on said wire in fluid communication with said lumen;
   a rotatable catheter rotatably mounted to said wire; and
   a flexible cutter assembly attached to said rotatable catheter and positioned to surround said balloon, said balloon being fluid inflatable to move said cutter assembly between a first configuration wherein said cutter assembly has a first radius of rotation and a second configuration wherein said cutter assembly has a second radius of rotation.

2. An atherectomy cutter as recited in claim 1 wherein said second radius of rotation is greater than said first radius of rotation.

3. An atherectomy cutter as recited in claim 1 further comprising inflation means operably connected with said lumen of said wire for inflating said balloon.

4. An atherectomy cutter as recited in claim 1 further comprising drive means operably connected with said torque tube for rotating said torque tube and said cutter assembly.

5. An atherectomy cutter as recited in claim 1 wherein said cutter assembly comprises:
   a grommet slidingly disposed over said wire distally from said balloon; and
   a plurality of cutting blades, each said blade having a proximal end attached to said rotatable catheter and a distal end attached to said grommet.

6. An atherectomy cutter as recited in claim 5 wherein said balloon simultaneously urges against a distal portion of each of said blades when said balloon is inflated.

7. An atherectomy cutter as recited in claim 5 wherein each said blade is formed with an advancing cutter segment on the distal portion of said blade, a withdrawing cutter segment on the proximal portion of said blade, and an intermediate segment therebetween.

8. An atherectomy cutter as recited in claim 5 comprising four blades, each said blade being diametrically opposed from another of said blades.

9. An atherectomy cutter as recited in claim 5 and further comprising a vacuum means coupled to said rotatable catheter for removing plaque cut by said cutting blades 10. An atherectomy cutter which comprises:
    a cutter assembly having a plurality of spaced apart blades, each said blade having a proximal end and a distal end, and said plurality of blades disposed to collectively define a hollow substantially ovoid shaped space;
    drive means for rotating said cutter assembly; and
    inflation means positioned in said ovoid space for moving said cutter assembly between a first configuration wherein said cutter assembly has a first radius of rotation and a second configuration wherein said cutter assembly has a second radius of rotation 11. An atherectomy cutter as recited in claim 10 wherein said second radius of rotation is greater than said first radius of rotation.

12. An atherectomy cutter as recited in claim 10 further comprising:
    a hollow wire formed with a lumen and said balloon is mounted on said wire in fluid communication with said lumen;
    means operably connected with said lumen of said wire for inflating said balloon;
    a rotatable catheter rotatably slidingly disposed over said wire; and
    drive means operably connected with said torque tube for rotating said torque tube and said cutter assembly.

13. An atherectomy cutter as recited in claim 12 wherein said cutter assembly comprises:
    a grommet slidingly disposed over said wire distally from said balloon; and
    a plurality of cutting blades, each said blade having a proximal end attached to said torque tube and a distal end attached to said grommet.

14. An atherectomy cutter as recited in claim 12 wherein each said blade is formed with an advancing cutter segment on the distal portion of said blade, a withdrawing cutter segment on the proximal portion of said blade, and an intermediate segment therebetween and wherein said balloon simultaneously urges against said distal segment of each of said blades when said balloon is inflated.

15. A method for using a balloon expandable atherectomy cutter which comprises the steps of:
    Providing an atherectomy cutter having a hollow wire formed with a lumen and an inflatable balloon mounted on said wire in fluid communication with said lumen, a rotatable catheter slidingly disposed over said wire, and a flexible cutter assembly attached to said rotatable catheter and positioned to surround said balloon, said balloon being fluid inflatable to move said cutter assembly between a first configuration wherein said cutter assembly has a first radius of rotation and a second configuration wherein said cutter assembly has a second radius of rotation;
    Inserting said atherectomy cutter into an artery of the patient and against plaque within a stenotic segment of the artery to be removed;
    Rotating said rotatable catheter and said cutter assembly in said first configuration to advance said cutter through said plaque;
    Inflating said balloon to move said cutter assembly into said second configuration; and
    Rotating said rotatable catheter and said cutter assembly in said second configuration and pulling said cutter through said plaque.

16. A method as recited in claim 15 wherein said atherectomy cutter includes a grommet slidingly disposed over said wire distally from said balloon and a plurality of cutting blades, each said blade having a proximal end attached to said rotatable catheter and a distal end attached to said grommet, and further, each said blade being formed with an advancing cutter segment on the distal portion of said blade, a withdrawing cutter segment on the proximal portion of said blade, and an intermediate segment therebetween.

17. A method as recited in claim 16 further comprising the step of simultaneously urging said balloon against a distal portion of each of said blades when said balloon is inflated.

18. A method as recited in claim 17 further comprising the step of removing plaque cut by the cutting blades with a vacuum means coupled to said rotatable catheter.

* * * * *